United States Patent
Wang et al.

(10) Patent No.: US 8,096,486 B2
(45) Date of Patent: Jan. 17, 2012

(54) AIR FRESHENER

(75) Inventors: Yuhua Wang, Beijing (CN); Lun Chai, Hong Kong (CN)

(73) Assignee: Winplus Company Limited, Shatin, N.T. (HK)

(*) Notice: Subject to any disclaimer, the term of this patent is extended or adjusted under 35 U.S.C. 154(b) by 621 days.

(21) Appl. No.: 12/281,569

(22) PCT Filed: Feb. 12, 2007

(86) PCT No.: PCT/CN2007/000492
§ 371 (c)(1),
(2), (4) Date: Sep. 3, 2008

(87) PCT Pub. No.: WO2007/101393
PCT Pub. Date: Sep. 13, 2007

(65) Prior Publication Data
US 2009/0010813 A1    Jan. 8, 2009

(30) Foreign Application Priority Data

Mar. 6, 2006   (CN) .......................... 2006 2 0007536
Apr. 26, 2006  (CN) .......................... 2006 2 0112987

(51) Int. Cl.
*A24F 25/00* (2006.01)
*A61L 9/04* (2006.01)
*B01D 11/04* (2006.01)
*B01D 47/16* (2006.01)
*B04B 5/00* (2006.01)
*C10J 1/18* (2006.01)

(52) U.S. Cl. ............................ 239/59; 239/58; 261/83

(58) Field of Classification Search ............ 239/58–59; 261/83
See application file for complete search history.

(56) References Cited

U.S. PATENT DOCUMENTS

| | | | |
|---|---|---|---|
| 5,029,756 A | | 7/1991 | Byrne |
| 5,180,107 A | * | 1/1993 | Lindauer .......................... 239/35 |
| 5,342,584 A | * | 8/1994 | Fritz et al. ...................... 422/124 |
| 5,492,675 A | * | 2/1996 | Brizard .......................... 422/122 |
| 5,805,768 A | * | 9/1998 | Schwartz et al. .............. 392/390 |
| 5,935,526 A | | 8/1999 | Moore |
| 6,080,367 A | | 6/2000 | Lin |
| 6,581,915 B2 | * | 6/2003 | Bartsch et al. .................. 261/26 |
| 6,790,408 B2 | * | 9/2004 | Whitby et al. ..................... 422/4 |
| 7,070,172 B2 | * | 7/2006 | Fabrega et al. ................. 261/30 |

FOREIGN PATENT DOCUMENTS

| | | |
|---|---|---|
| CN | 2322615 Y | 6/1999 |
| CN | 2323788 Y | 6/1999 |
| CN | 2348851 Y | 11/1999 |
| CN | 2354572 Y | 12/1999 |
| WO | 03074096 A1 | 9/2003 |

* cited by examiner

*Primary Examiner* — Walter Griffin
*Assistant Examiner* — Christopher Vandeusen
(74) *Attorney, Agent, or Firm* — The Webb Law Firm

(57) ABSTRACT

An air freshener of the invention includes a rotating box, a fixed base disposed on the rotating box, the rotating box rotating with respect to the fixed base, and a perfume box filled with a perfume, which can rotate with the rotating box. The rotating box has an annular shape in cross section and has an internal space for receiving and embedding the perfume box therein. Air holes are formed in the fixed base for exposing a portion of the perfume box when the rotating box is rotated with respect to the fixed base. The air freshener of the invention is applicable to be used inside a car or a room, and is capable of both refreshing the air and adjusting the release amount of the diffused perfume vapor.

4 Claims, 8 Drawing Sheets

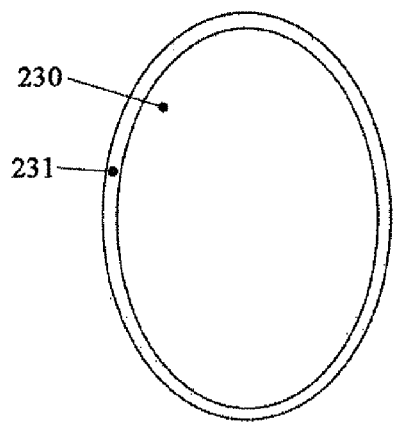
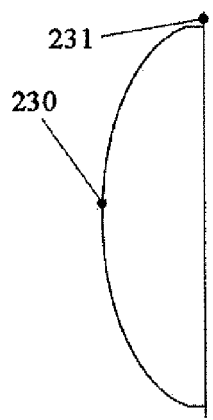
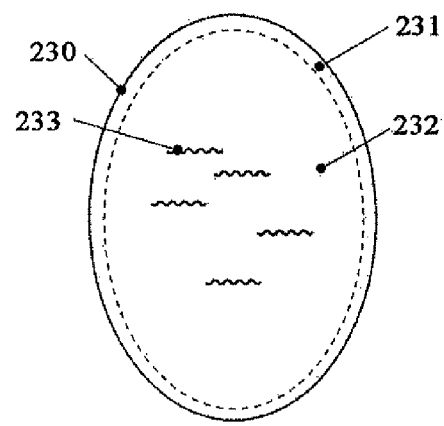
FIG. 11 (a)   FIG. 11 (b)   FIG. 12
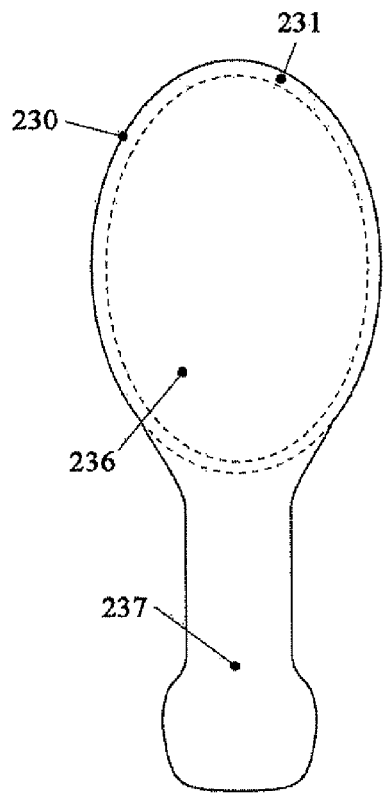
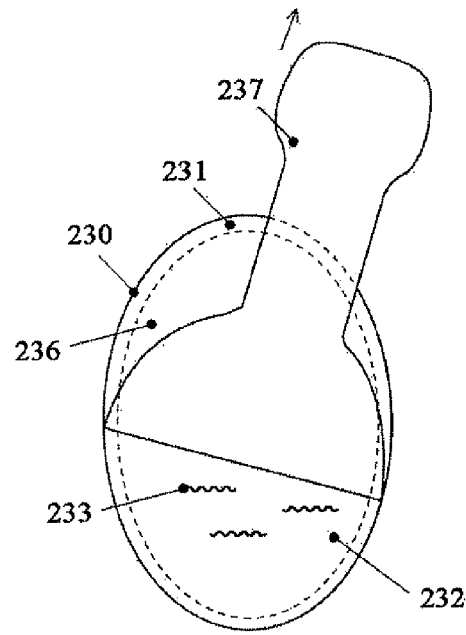
FIG. 13 (a)   FIG. 13 (b)

AIR FRESHENER

FIELD OF THE INVENTION

The present invention relates to an air freshener.

BACKGROUND OF THE INVENTION

Nowadays an air freshener is used in many places such as inside a room, or in a car etc., and there are various air fresheners in the market. However, these air fresheners have various defects. For instance, a conventional air freshener can not adjust the release amount of a perfume vapor, thereby making the fragrance inside a room or a car either too strong or too weak to achieve the object of refreshing the air.

SUMMARY OF THE INVENTION

The object of the present invention is to provide a novel air freshener which can overcome the defects existing in the prior art and adjust the release amount of the perfume vapor.

Accordingly, the air freshener of the present invention includes: a rotating box, a fixed base which is fixed on the rotating box, the rotating box rotating with respect to the fixed base, a perfume box which is filled with a perfume and rotates together with the rotating box, wherein the rotating box has an annular shape in its cross section and has an internal space for receiving and embedding the perfume box therein, and air holes are formed in the fixed base for exposing a portion of the perfume box when the rotating box rotates with respect to the fixed box.

In accordance with one aspect of the air freshener of the present invention, the rotating box has a substantially spherical protrusion which forms a space for receiving and embedding the perfume box therein. A side of the rotating box which is opposite to the protrusion is opened and the fixed base is fixed on the opened side. The fixed base is a circular sheet molded from thermoplastics. The rotating box is also molded from thermoplastics. The opened side of the rotating box has a recessed step and a step surface. The circular sheet is embedded into the recessed step of the rotating box and abuts against the step surface, so that the rotating box can rotate with respect to the circular sheet. At least one fastener is formed on an annular edge of the rotating box, so as to fix the fixed base on the rotating box and prevent the fixed base from dropping off. Two fixed fasteners and one movable fastener may be formed on the annular edge of the rotating box, and two slots are formed on both sides of the movable fastener. After being fixed to the two fixed fasteners, the fixed base is embedded and locked into the fixed fasteners by pulling the movable fastener and then loosening the movable fastener.

In accordance with another aspect of the air freshener of the present invention, the rotating box consists of a front cover and a rear base having a round groove thereon for receiving the fixed base. A recessed step and a step surface are formed on the front cover, and the rear base is embedded into the step of the rotating box and abuts against the step surface. Air holes are formed in the round groove of the rear base, so as to expose a portion of the perfume box. When the rotating box rotates with respect to the fixed base, a portion of the perfume box can be viewed through the air holes of the fixed base and the air holes in the round grooves of the rear base. The front cover and the rear base are connected by fasteners, the round groove of the rear base and the fixed base are connected by fasteners. The external contour of the front cover, the rear base and the perfume box body may be elliptic.

The perfume box has a box body formed by suction molding from transparent plastic sheet material, a semipermeable film which can seal a liquid perfume and diffuse a perfume vapor, and an aluminum foil film which can prevent the diffusing of the perfume vapor before being used. The perfume box is embedded into the step of the rotating box and abuts against the step surface, and the perfume box is in a shape adaptive to the rotating box, so as to facilitate the perfume box to be embedded into the rotating box and to rotate together with the rotating box. Preferably, the rotating box has grids extending towards the interior of the annular space of the rotating box at the opposite two ends of the protrusion and protruding tips which are formed at an angle with respect to the grids. The perfume box has a shape adaptive to the rotating box, and has a recessed portion corresponding to the grids and the protruding tips so as to facilitate the perfume box to be embedded into the rotating box and to rotate together with the rotating box.

In addition, the air freshener of the present invention may include a fixing device used for fixing an assembled air freshener on a surface of a place using the air freshener. There is a clipping groove on the back side of the fixed base for clipping the fixing device. The fixing device may be a fixing clip which is made of hard plastics, or a suction cup which is made of soft plastics.

The air freshener of the present invention, which has overcome the defects existing in the prior art and is suitable to be used inside a car or a room for freshening the air therein, can adjust the release amount of the diffused perfume vapor, thereby reducing the costs and increasing the economic benefits significantly.

BRIEF DESCRIPTION OF THE DRAWINGS

FIG. 1(a) is a front view of the rotating box; FIG. 1(b) is a back view of the rotating box; FIG. 1(c) is a partial view along line A-A of the rotating box; FIG. 1(d) is a sectional view along line C-C of the rotating box; FIG. 1(e) is a sectional view along line D-D of the rotating box; FIG. 1(f) is a sectional view along line E-E of the rotating box; and FIG. 1(g) is a sectional view along line G-G of the rotating box.

FIG. 2(a) is a front view of the fixed base; FIG. 2(b) is a back view of the fixed base; FIG. 2(c) is a sectional view along line H-H of the fixed base; and FIG. 2(d) is a partial view along line K-K of the fixed base.

FIG. 3(a) is a schematic view of a fixing clip 22; FIG. 3(b) is a schematic view of a suction cup 23; and FIG. 3(c) is a partial view along line R-R of the suction cup 23.

FIG. 4(a) shows a box body 30 of the perfume box; FIG. 4(b) is a view along line M-M of the box body 30 of the perfume box; and FIG. 4(c) is a view along line N-N of the box body 30 of the perfume box.

FIG. 6(a) is a schematic view of the perfume box having a sealing aluminum foil laminated to a sealing film, and FIG. 6(b) is a schematic view of the perfume box from which the aluminum foil is being torn off.

FIG. 7(a) is a front schematic view of the air freshener after having the perfume box embedded into the rotating box; FIG. 7(b) is a back schematic view of the air freshener after having the perfume box embedded into the rotating box; FIG. 7(c) is a back schematic view of FIG. 7(b), after a circular sheet 16 of said fixed base is putting thereon.

FIG. 8(a) is a front view of a front cover 201 of the rotating box; FIG. 8(b) is a back view of the front cover 201 of the rotating box; FIG. 8(c) is a sectional view along line A-A of the front cover 201; and FIG. 8(d) is a sectional view along line B-B of the front cover 201.

FIG. 9(a) is a front view (toward the interior of the rotating box) of the rear base 202 of the rotating box; FIG. 9(b) is a back view (toward exterior of the rotating box, and being backward with respect to the whole air freshener) of the rear base 202 of the rotating box, FIG. 9(c) is a sectional view along line C-C of the rear base 202 of the rotating box; FIG. 9(d) is a sectional view along line D-D of the rear base 202 of the rotating box; FIG. 9(e) is a sectional view along line E-E of the rear base 202 of the rotating box; FIG. 9(f) is an enlarged view of a movable fastener 210 of the rear base 202 of the rotating box; FIG. 9(g) is a partial view of a latch 211 of the movable fastener 210 of the rear base 202 of the rotating box; FIG. 9(h) is a sectional view along line F-F of the movable fastener 210 of the rear base 202 of the rotating box; FIG. 9(i) is a sectional view along line G-G of the movable fastener 210 of the rear base 202 of the rotating box; and FIG. 9(j) is a sectional view along line H-H of the latch 211 of the movable fastener 210 of the rear base 202 of the rotating box.

FIG. 10(a) is a back view (toward exterior of the rotating box, and being backward with respect to the whole air freshener) of the fixed base 216; and FIG. 10(b) is a sectional view along line K-K of the fixed base 216.

FIG. 11 is a schematic view of a box body 230 of a perfume box of a second embodiment of the present invention. FIG. 11(a) is a schematic view of the box body 230 of the perfume box of the second embodiment of the present invention; FIG. 11(b) is a side view of the box body 230 of the perfume box.

FIG. 12 is a schematic view of a perfume box of a second embodiment of the present invention in the state of being used.

FIG. 13 is a schematic view of a perfume box of a second embodiment of the present invention. FIG. 13(a) is a schematic view of the perfume box of the second embodiment of the present invention sealed with an aluminum foil film before being used; FIG. 13(b) is a schematic view of the perfume box of the second embodiment of the present invention from which the aluminum foil film is being torn off for preparation of being used.

DETAILED DESCRIPTION OF THE PREFERRED EMBODIMENTS

The embodiments of the present invention are described below in accordance with the drawings.

Figure 6:
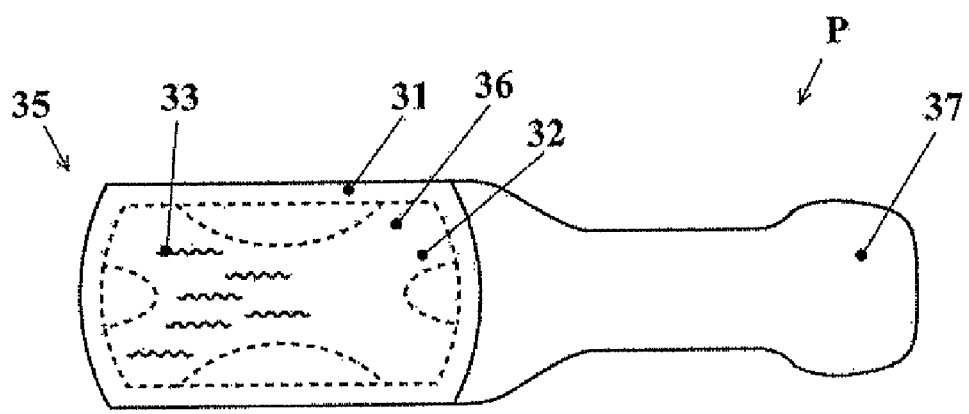
FIG. 6 is a schematic view of a perfume box of an air freshener of a first embodiment of the present invention.
Figure 6:
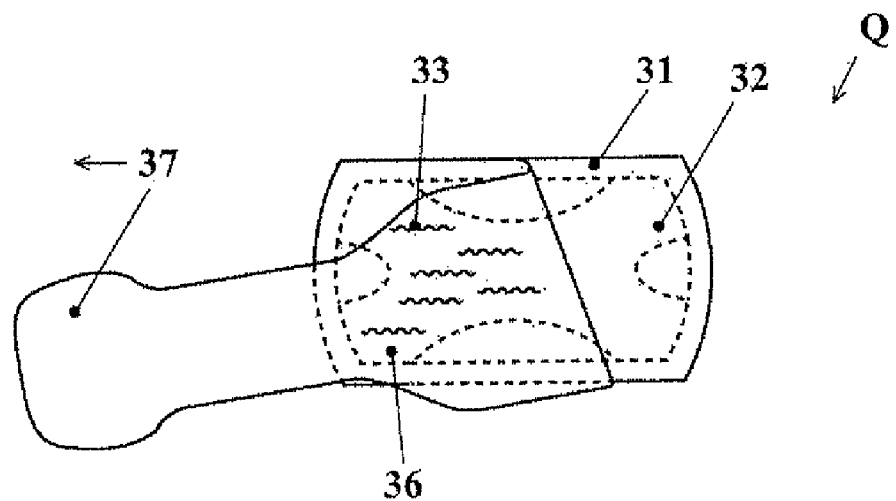

An air freshener of a first embodiment of the present invention includes a rotating box F1 as shown in FIG. 1(a) or B1 as shown in FIG. 1(b), a fixed base F2 as shown in FIG. 2(a) or B2 as shown in FIG. 2(b), and a perfume box P filled with a perfume as shown in FIG. 6(a) or Q as shown in FIG. 6(b). The rotating box F1 or B1 has a side which can be opened, therefore, the rotating box can also be called as "a rotating cover". The fixed base F2 is fixed on the rotating box and closes the opened side of the rotating box.

The rotating box may be made of any kind of plastic material, preferably being made of polypropylene. The rotating box may be molded from thermoplastics. As shown in FIG. 1(a) and FIG. 1(b), said rotating box is in an annular shape. As shown in FIG. 1(a), FIG. 1(b), FIG. 1(c) and FIG. 1(d), said rotating box has grids 3 and protruding tips 4 extending towards an interior of an annular space of said rotating box, and has a substantially spherical protrusion which forms a space for receiving and embedding a perfume box P or Q shown in FIG. 6(a) and FIG. 6(b).

FIG. 2(a) is a front view of a fixed base of an air freshener of a first embodiment of the present invention, in which a reference sign F2 denotes the fixed base. FIG. 2(b) is a back view of the fixed base, in which a reference sign B2 denotes the fixed base. Said fixed base is molded from thermoplastics, and has a circular sheet 16 as a main body thereof and two air holes 17 thereon. The number of the air holes may be one or more than one, The air holes may have a shape other than the substantially rectangular shape shown in FIG. 2(a) and FIG. 2(b). A clipping groove 18 can be viewed from FIG. 2(b) and FIG. 2(c) which are a back view and a sectional view along H-H direction of the fixed base respectively. The clipping groove 18 is used for clipping a fixing clip 22 or a suction cup 23 shown in FIG. 3. A protruding point 19 can be viewed from FIG. 2(d) which is a partial view along K-K direction of the fixed base. The protruding point 19 is used for restricting a rotating angle when a rotating box shown in FIG. 1 rotates.

Figure 1:
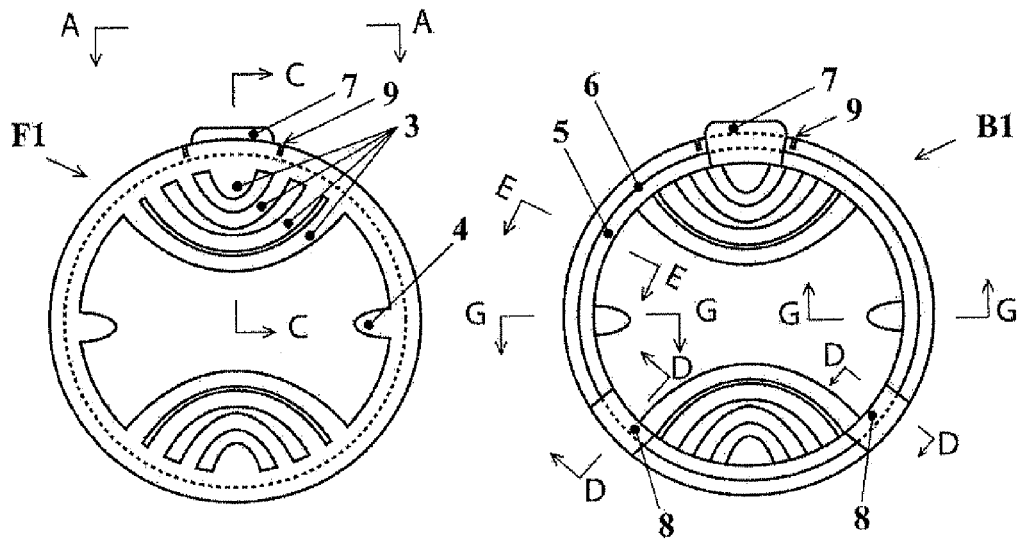
FIG. 1 is a schematic view of a rotating box of an air freshener of a first embodiment of the present invention.
Figure 1:
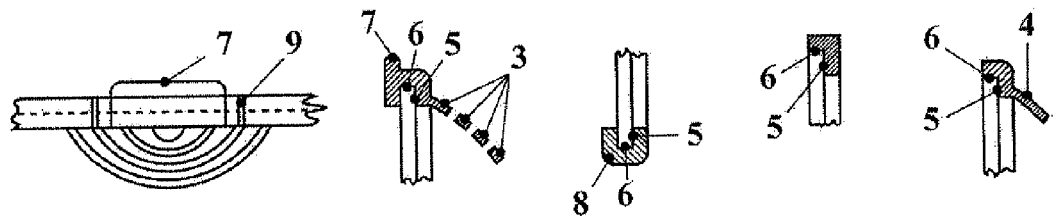
Figure 2:
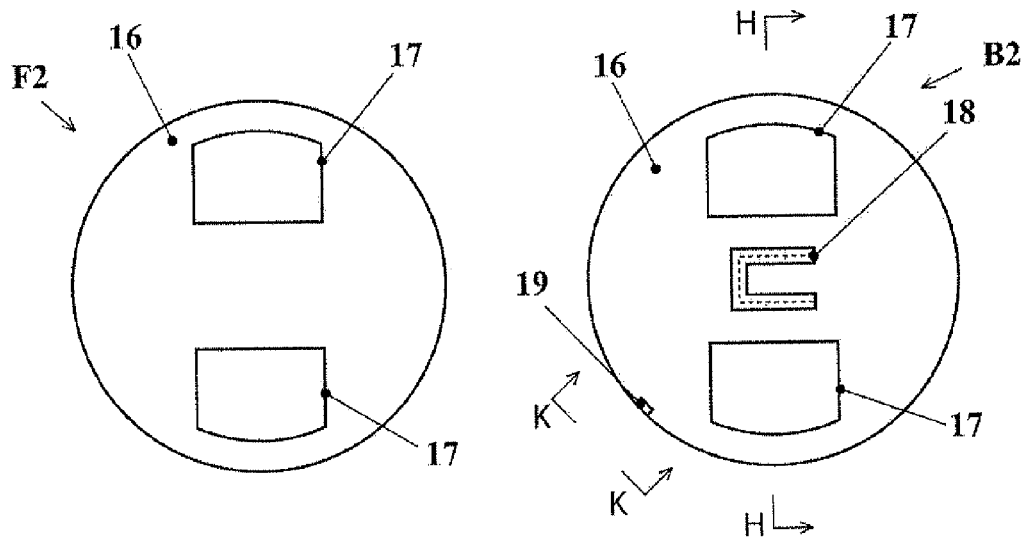
FIG. 2 is a schematic view of a fixed base of an air freshener of a first embodiment of the present invention.
Figure 2:
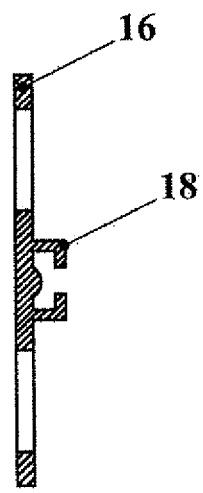
Figure 2:
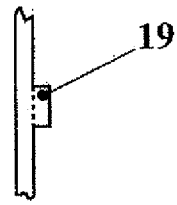

As shown in FIG. 1(b) and FIG. 1(d), the rotating box F1 (or B1) comprises a recessed step (step ring) 6 and a step surface 5. The circular sheet 16 of said fixed base has a diameter slightly less than that of the step ring 6 of said rotating box shown in FIG. 1, so that the circular sheet 16 can be just placed inside the step ring 6 and be turned around by hand. While being placed, the circular sheet 16 just abuts against the step surface 5 of said rotating box.

In order to place said fixed base B2 inside the step ring 6 and prevent said fixed base B2 from dropping off, two fixed fasteners 8 (one or more than two fixed fasteners are also acceptable, although they are not shown in the drawings) and one movable fastener 7 (a plurality of movable fasteners are also acceptable, although they are not shown in the drawings) are provided on said rotating box shown in FIG. 1. Two slots 9 (one or more than two slots are also acceptable, although they are not shown in the drawings) are formed on both sides of the movable fastener 7 and are located on an external ring of the rotating box, and enable the plastic material there to be pulled thus to be deformed and shifted, and then to be restored to its original shape by using the resilience thereof. When said fixed base is placed inside said rotating box, the circular sheet 16 is firstly clipped inside the two fixed fasteners 8 (more than two fixed fasteners are also acceptable, although they are not shown in the drawings) and is caused to abut against the step ring 6 and the step surface 5, and then the movable fastener 7 is pulled to cause the circular sheet 16 there to be embedded into and abut against the step ring 6 and the step surface 5, and then the movable fastener 7 is loosened to cause said fixed base B2 to be clipped there as well. In this way, since being clipped at three points 7, 8, 8, said fixed base can not drop off, and said rotating box can rotate with respect to said fixed base B2. What has been described here is only one example of a method of combining said rotating box and said fixed base, and it is a matter of course that other alternative methods can be employed, for example, the method in which a "sliding-in and back-buckling" type fastener is made there-between for clipping said rotating box and said fixed base together (not shown in the drawings).

In addition, the grids 3 and the protruding tips 4 on said rotating box can also be formed in other shapes, however, a convex-concave shape of the box body of said perfume box corresponding to the grids 3 and the protruding tips 4 must correspond to those of the grids and the protruding tips, so that the box body of said perfume box and the grids 3 and the protruding tips 4 are interbedded (inserted) together, and said rotating box rotates together with the box body of said perfume box (not shown in the drawings).

As shown in FIG. 3(a), a clip head 24 of said fixing clip 22 is embedded into the clipping groove 18 of said fixed base, said fixing clip 22 is generally made of hard plastic material (or other plastic material), and a clip tooth 25 of said fixing clip 22 may be clipped on grilles of an air outlet of an air conditioner of a car so as to cause a fixing device shared by the air fresheners in the first and the second embodiments of the present invention to be fixed there. In the meantime, a perfume vapor emitted by the air freshener can be diffused with the help of wind blown from the air outlet of the air conditioner.

As shown in FIG. 3(b), the suction cup 23 is made of soft plastic material (such as polyvinyl chloride), one end of the suction cup 23 is the clip head 24, and the other end of the suction cup 23 is a "vacuum cup" 26. The clip head 24 is embedded into the clipping groove 18 of said fixed base, the "vacuum cup" 26 at the other end of the suction cup 23 can cause the air freshener of the present invention to be attached on a smooth surface such as a surface of window glass inside a car, or any smooth surface inside a room.

The above-mentioned components are generally molded from thermoplastics by injection molding. Said suction cup 23 is generally made of soft plastic material (such as polyvinyl chloride), other components are generally made of hard plastic material such as ABS, polystyrene, polypropylene, nylon and polyester etc.

Figure 4:
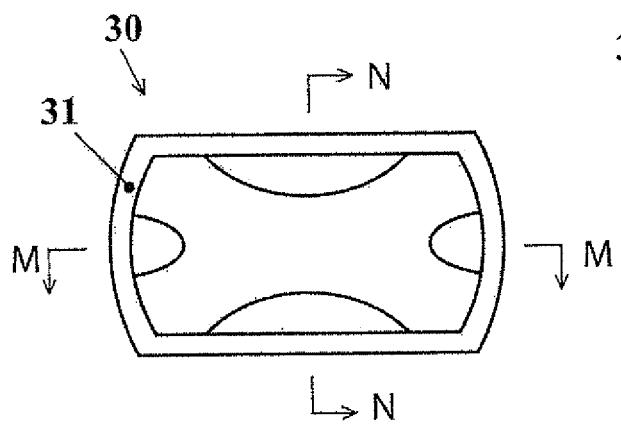
FIG. 4 is a schematic view of a box surface of a perfume box of an air freshener of a first embodiment of the present invention.
Figure 4:
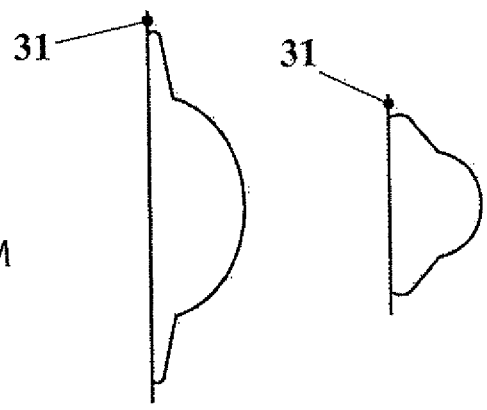
Figure 4:
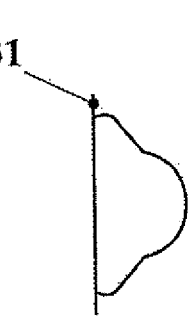

As shown in FIG. 4(a) to FIG. 4(c), the box body 30 of the perfume box of the air freshener of the first embodiment of the present invention is substantially in a protruding spherical shape. The box body 30 is generally formed by "bubble cap" type suction molding from transparent plastic sheet material such as polyester or polyvinyl chloride, although other plastic material can be used. Preferably, polyester sheet material is used in order to prevent reaction with chemical substance of a perfume. A consumer can view a liquid perfume inside the perfume box through a transparent material used for making the perfume box. After being finished, the box body 30 has an edge 31 at a same plane, arc-shaped extension lines at both ends of the edge 31 that constitute a circle which matches with the step ring 6 and the step surface 5 of said rotating box, and can be placed inside the step. The box body 30 is substantially in a protruding spherical shape, and a protruding height of which is reduced (slightly recessed with respect to the spherical shape) at a position corresponding to the grids 3 and the protruding tips 4 of said rotating box so as to make the recessed part of the box body 30 to be interbedded together with the grids 3 and the protruding tips 4, thereby the box body 30 of the perfume box can be driven to rotate together with the rotating box so as to adjust the opening area of the box body 30, i.e. to adjust the releasing area of the perfume.

Figure 5:
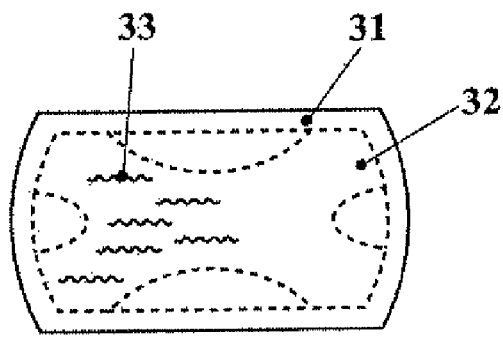
FIG. 5 is a schematic view of a perfume box of an air freshener of a first embodiment of the present invention filled with a liquid perfume and sealed with a plastic film.

As shown in FIG. 5, the box body 30 is sealed by a layer of extremely-thin semipermeable film 32 laminated along the whole plane of the edge 31 so as to form a closed space in which a liquid perfume 33 is filled inside the box body 30. Said semipermeable film 32 has a characteristic of preventing the liquid perfume 33 leaking from the box body 30, and diffuse the gaseous perfume molecules which have been volatilized so that scent of the perfume gas can be smelt outside the box body 30. Said semipermeable film 32 may be any type of a film with any size in conformity with the above requirements, for example, a polythene or special polyethylene film with a thickness of about 0.015 mm.

Figure 3:
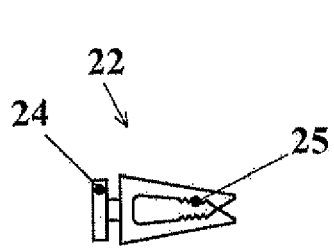
FIG. 3 is a schematic view of a fixing device (a fixing clip and a suction cup) of an air freshener used in both a first embodiment and a second embodiment of the present invention.
Figure 3:
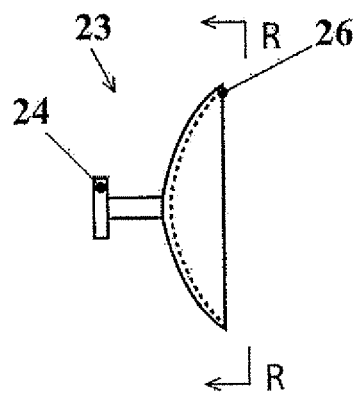
Figure 3:
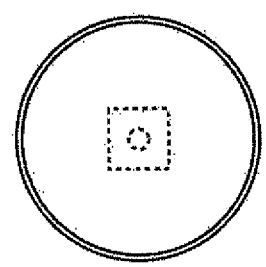

When using the air freshener of the first embodiment of the present invention, the perfume box in which the liquid perfume 33 has been housed and which has been sealed by the semipermeable film 32 is firstly embedded into the interior space formed in the rotating box, then the arc-shaped portions at both ends of the edge 31 of the box body 30 is embedded into the step ring 6 and the step surface 5 of the rotating box, then the circular sheet 16 of said fixed base is embedded into two fixed fasteners 8 (more than two fixed fasteners are also acceptable, although they are not shown in the drawings), and then the other end of the circular sheet 16 is also embedded into the step ring 6 of the rotating box by pulling the movable fastener 7. At this time, as viewed from the back of the air freshener the semipermeable film 32 which diffuses the perfume vapor has been covered by the circular sheet 16, and the perfume vapor can not be released or can only be released a little from the apertures between the semipermeable film 32 and the circular sheet 16 when they are moved with respect to each other. This is a state in which the air freshener is not used. When the rotating box is rotated, the box body 30 of the perfume box is driven to rotate at an angle of about 90° (or at other rotating angles) together with the rotating box. At this time, the two air holes on the circular sheet 16 are aligned with the surface of the semipermeable film 32 and the perfume vapor can be released from said two air holes. The releasing area of the perfume vapor can be increased or reduced by adjusting the rotating angle of the rotating box so as to adjust the release amount of the perfume vapor. The position of the protruding point 19 on the circular sheet 16 (FIG. 2) is designed so that the release of the perfume vapor is completely closed when the protruding point 19 is rotated to an end to abut against one of the fixed fasteners 8, and the perfume vapor is released to the maximum extent when the protruding point 19 is rotated to the other end. The air holes 17 of said fixed base may also be in other shapes. At this time, said fixing clip 22 in FIG. 3 is then mounted thereon, so that the air freshener of the present invention can be clipped on grilles at an air outlet of an air conditioner of a car so as to cause the emitted perfume vapor to be diffused with the help of the blowing wind of the air conditioner, or said suction cup 23 in FIG. 3 is then mounted thereon, so that the air freshener of the first embodiment of the present invention can be fixed on a smooth surface such as a surface of window glass inside a car, or any smooth surface inside a room.

FIG. 6(a) shows the state in which the perfume box of the air freshener of the first embodiment of the present invention to be used after being produced, and a reference sign P in FIG. 6(a) denotes the perfume box in the state. Since it usually takes a quite long time from the perfume box being produced to the perfume box being used by a consumer, a layer of airtight aluminum foil film 36 is additionally laminated to the semipermeable film 32 in order to prevent the perfume to be volatilized and released from the perfume box before being used. The aluminum foil film 36 is also laminated to the semipermeable film 32 along the edge 31 of the box body 30.

A long tail 37 is provided on the aluminum foil film 36 in order to facilitate the aluminum foil film 36 to be torn off when the perfume box is used. The condition when the sealing and the laminating are performed is controlled so that the semipermeable film 32 is laminated to the edge 31 of the box body 30 firmly so as not to be torn off, while the aluminum foil film 36 is laminated to the semipermeable film 32 moderately, so as to be easily torn off from the semipermeable film 32 without damaging the sealing between the semipermeable film 32 and the edge 31 of the box body 30. FIG. 6(b) shows the perfume box of the first embodiment of the present invention from which the aluminum foil film 36 is being torn off, and a reference sign Q denotes the perfume box in the state in which the aluminum foil film 36 is being torn off.

For the consumer's convenience, the perfume box may be placed in the space formed by the rotating box and the fixed base in the factory, and the long tail 37 of the aluminum foil film 36 should be folded back at this time, leaving a short portion of the long tail 37 outside the perfume box. Immediately before starting to use the perfume box, the consumer may pull the short portion of the long tail 37 so as to tear off the aluminum foil film 36 while keeping the perfume box inside the rotating box.

Figure 7:
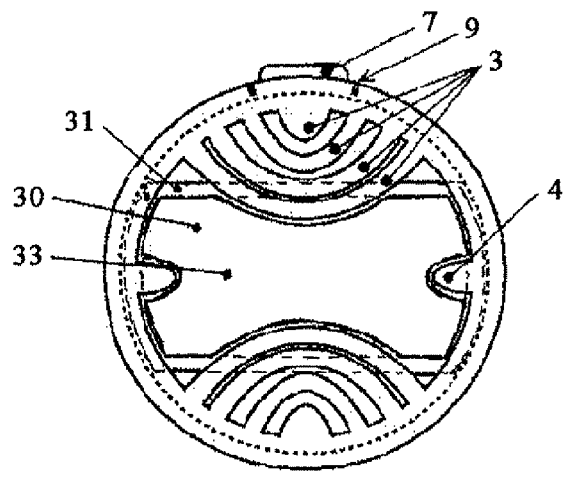
FIG. 7 is a schematic view of a structure of an air freshener of a first embodiment of the present invention.
Figure 7:
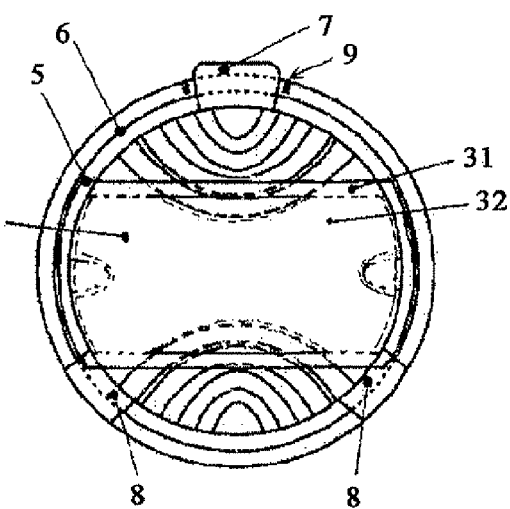
Figure 7:
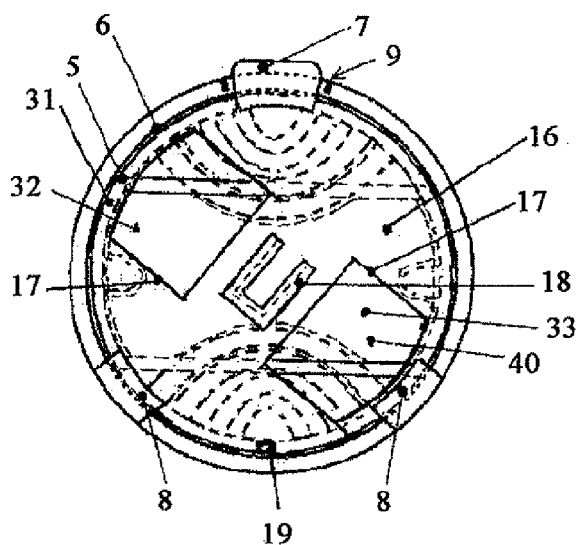
Figure 8:
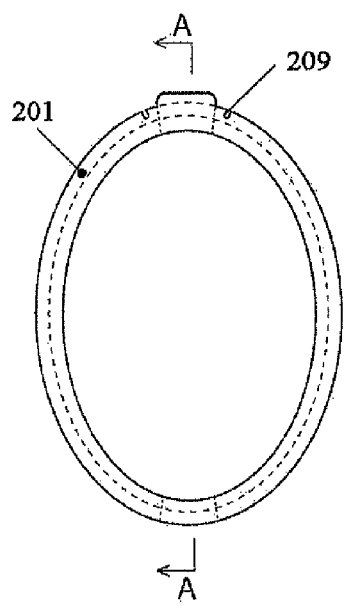
FIG. 8 is a schematic view of a front cover of a rotating box of an air freshener of a second embodiment of the present invention.
Figure 8:
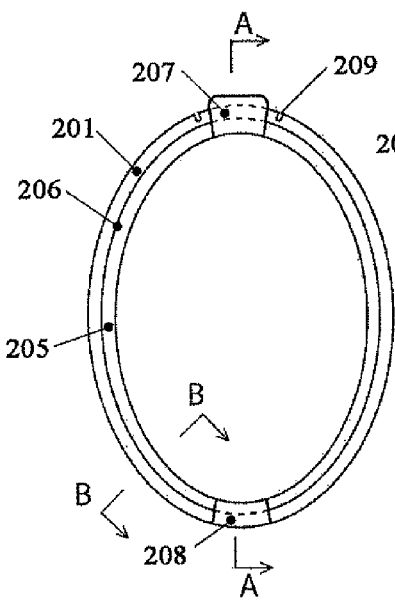
Figure 8:
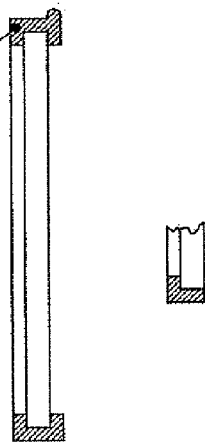

As shown in FIG. 7(a) to FIG. 7(c), the protruding spherical surface and each of the recessed portions of the box body 30 of the first embodiment of the present invention are just interbedded together with the grids 3 and the protruding tips 4 of the rotating box, and the arc-shaped portions at both ends of the plane of the edge 31 of the box body 30 are just placed inside the step ring 6 and abut against the step surface 5 of said rotating box. Accordingly, the box body 30 can be driven to rotate together with the rotating box when the rotating box rotates.

One end of said fixed base of the first embodiment of the present invention is firstly clipped into the two fixed fasteners 8 of said rotating box, and at this time the protruding point 19 should be placed just between the two fixed fasteners 8, then the movable fastener 7 is pressed to make said fixed base to be embedded into the step ring 6 and abut against the step surface 5, and then the movable fastener 7 is loosened to make said fixed base to be clipped by the three fasteners 7, 8 and 8. In this way, said rotating box is able to rotate freely with respect to said fixed base, while said fixed base will not drop off. Since the protruding point 19 is located between the two fixed fasteners 8, a rotating range thereof is restricted. In FIG. 7(c), the protruding point 19 is located in an approximately middle point of the two fixed fasteners 8, at this time the air holes 17 of said fixed base cause a portion of the semipermeable film 32 laminated on said perfume box (i.e. the portion denoted by reference sign 40 in FIG. 7(c)) to be exposed, and the perfume vapor can be released from said air holes 17. When the protruding point 19 is rotated close to the right fastener 8, the two air holes 17 are entirely aligned with the releasing surface of the perfume, and thereby the perfume vapor is released to the maximum extent. When the protruding point 19 is rotated close to the left fastener 8, the releasing surface of the perfume is entirely covered by said fixed base, and thereby the perfume vapor is completely closed or released to the minimum extent. The clipping groove 18 is provided in the middle part of said fixed base 16, and is used for clipping the fixing clip 22 or the suction cup 23.

As shown in FIG. 8(a) to FIG. 8(d), a reference sign 201 denotes a front cover of the rotating box of the air freshener of the second embodiment of the present invention. The front cover 201 which is molded by injection molding from thermoplastics (or other materials) is substantially in elliptical shape (or in other shapes, although not shown in the drawings). A recessed step 205 is provided around the periphery in substantially elliptical shape (or in other shapes, although not shown in the drawings) of the front cover 201 of said rotating box, thus a step surface 206 is formed. A reference sign 208 denotes a fixed fastener for mounting a rear base 202, and a reference sign 207 denotes a movable fastener which uses two slots 209 (one or more than two slots are also acceptable, although they are not shown in the drawings) formed on an edge of the movable fastener 207 to cause the plastic material there to be pulled thus to be deformed, thereby making the rear base 202 to be embedded, and then to be restored to its original shape by using the resilience of the plastic material itself, thereby making the rear base to be clipped firmly.

Figure 9:
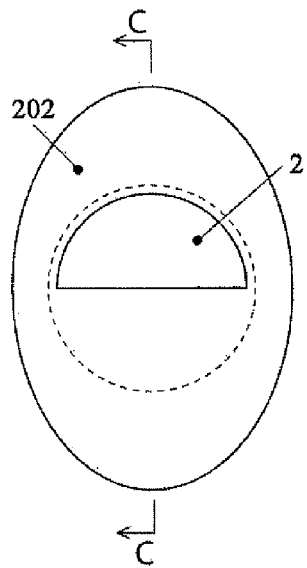
FIG. 9 is a schematic view of a rear base 202 of a rotating box of an air freshener of a second embodiment of the present invention.
Figure 9:
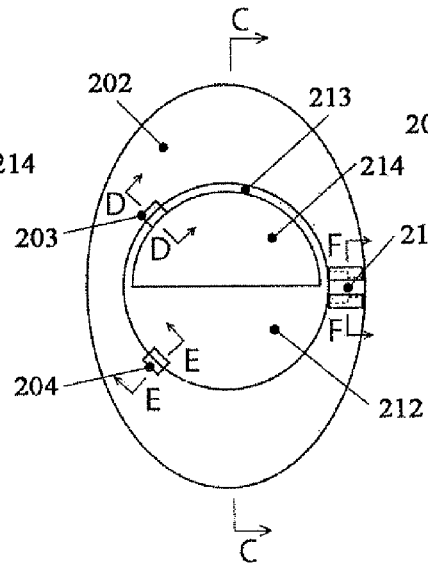
Figure 9:
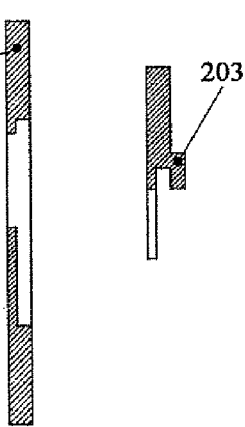
Figure 9:
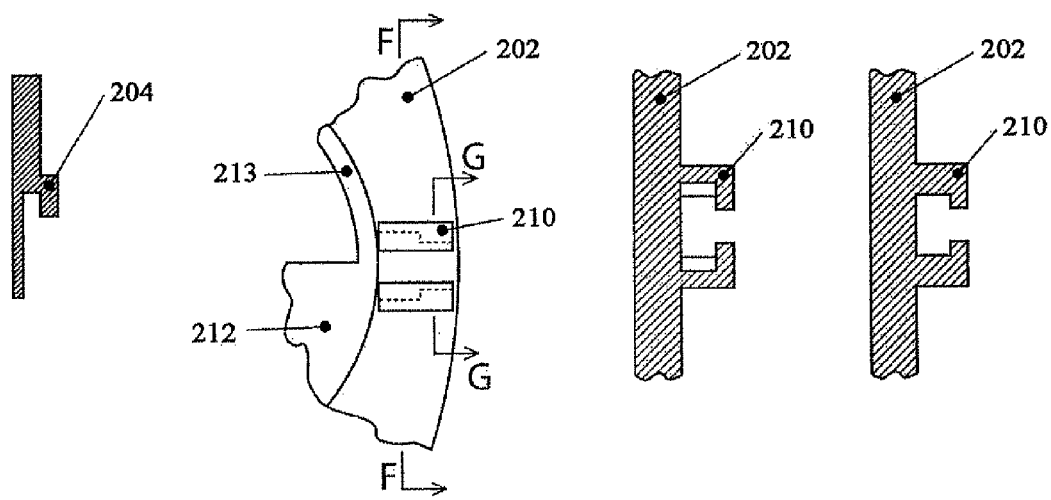

As shown in FIG. 9(a) to FIG. 90), the rear base 202 of the rotating box of the air freshener of the second embodiment of the present invention is molded by injection molding from thermoplastics (or other materials) and is substantially in elliptical shape (or in other shapes, although not shown in the drawings). The rear base 202 of said rotating box has an external shape and a size matching with the recessed step 205 and the step surface 206 of said front cover 201 of said rotating box in FIG. 8, and can be put into the recessed step 205. As shown in FIG. 9(b), a round groove 213 is provided in a suitable part (in the central part as shown in FIG. 9(b), other parts are also acceptable, although they are not shown in the drawings) of the rear base 202 of said rotating box for receiving a fixed base 216. Said round groove 213 is not penetrated through, leaving a plane 212 unchanged. Air holes 214 are provided in said round groove 213 which are penetrated and said round groove 213 forms a step for receiving said fixed base 216. Said air holes 214 are substantially in semicircular shapes (other shapes are also acceptable, although they are not shown in the drawings). Reference signs 203 and 204 denote two fixed fasteners (more than two fixed fasteners are also acceptable, although they are not shown in the drawings), and a reference sign 210 denotes one movable fastener (a plurality of movable fasteners are also acceptable, although they are not shown in the drawings). When said fixed base 216 is placed, the fixed base 216 is firstly made to abut against the fixed fasteners 203 and 204, then placed in the movable fastener 210, and then the latch 211 is added. In this way, said fixed base 216 will be fixed firmly, and can rotate with respect to said rear base 202. Said front cover 201 and said rear base 202 are connected by using the fasteners, and the round groove 213 of said rear base 202 and said fixed base 216 are connected by using the fasteners as well.

Figures 9, 10:
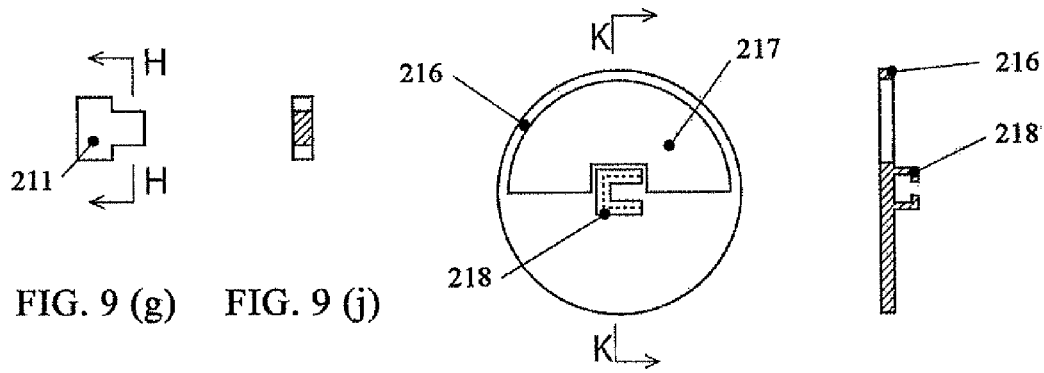
FIG. 10 is a schematic view of a fixed base 216 of an air freshener of a second embodiment of the present invention.

As shown in FIG. 10(a) to FIG. 10(b), said fixed base 216 is a circular plastic (or other materials) sheet which has an external shape and a size matching with the round groove 213 of the rear base 202 of said rotating box in FIG. 9(b), can be put into the round groove 213 in a place abutting against the plane 212, and can be rotated. When said fixed base 216 is placed, said fixed base 216 is firstly made to abut against the fixed fasteners 203 and 204, and is laid in a plane, and then the latch 211 is added to the movable fastener 210. In this way, said fixed base 216 will be fixed firmly, and can rotate with respect to said rear base 202. After removing the latch 211, said fixed base 216 will be loosened. Said fixed base 216 has air holes 217 which are substantially in semicircular shape (other shapes are also acceptable, although they are not shown in the drawing). Said rotating box and said fixed base 216 constitute a box which can contain said perfume. A clipping groove 218 is provided in the middle part of said fixed base 216, and is used for clipping the fixing device including the fixing clip 22 or the suction cup 23.

As shown in FIG. 11(a) to FIG. 11(b), a box body 230 is generally formed by "bubble cap" type suction molding from transparent plastic sheet material such as polyester or polyvinyl chloride, although other plastic material can be used. Preferably, polyester sheet material is used in order to prevent reaction with the perfume of a chemical substance. A consumer can view a liquid perfume inside the perfume box through a transparent material used for making the box body 230. After being finished, the box body 230 has an edge 231 at a same plane, and has a shape and a size in the periphery matching with the recessed step 205 and step surface 206 of said front cover 201 in FIG. 8(b), so as to be placed inside the step 205 and the step surface 206. A protruding surface of said box body 230 may be a spherical surface or an ellipsoidal surface (other shapes are also acceptable, although they are not shown in the drawings), so as to be adaptive to the interior space contour of said rotating box.

As shown in FIG. 12, said box body 230 of the perfume box has an external contour in an elliptic shape (other shapes are also acceptable, although they are not shown in the drawings). Said box body 230 is seated by a layer of extremely-thin semipermeable film 232 laminated along the whole plane of the edge 231 thereof so as to form a closed space in which a liquid perfume 233 is filled inside the box body 230. Said semipermeable film 232 has a characteristic of preventing the liquid perfume 233 leaking from the box body 230, and diffuses the gaseous perfume molecules which have been volatilized so that the scent of the perfume vapor can be smelt outside the box body 230. Said semipermeable film 232 may be any type of a film with any size in conformity with the above requirements, for example, a polythene or special polyethylene film with a thickness of about 0.015 mm.

FIG. 13(a) shows the state in which the perfume box of the air freshener of the second embodiment of the present invention to be used after being produced. Since it usually takes a quite long time from the perfume box being produced to the perfume box being purchased and used by a consumer, a layer of an airtight aluminum foil film 236 is additionally laminated to the semipermeable film 232 in order to prevent the perfume to be volatilized and released from the perfume box before being used. The aluminum foil film 236 is also laminated to the semipermeable film 232 along the edge 231 of the box body 230. A long tail 237 is provided on the aluminum foil film 236 in order to facilitate the aluminum foil film 236 to be torn off when the perfume box is used. The condition when the sealing and the laminating are performed is controlled so that the semipermeable film 232 is laminated to the edge 231 of the box body 230 firmly, so as not to be torn off, while the aluminum foil film 236 is laminated to the semipermeable film 232 moderately, so as to be easily torn off from the semipermeable film 232 without damaging the sealing between the semipermeable film 232 and the edge 231 of the box body 230. FIG. 13(b) shows the perfume box from which the aluminum foil film 236 is being torn off.

For the consumer's convenience, the perfume box may be placed in the space formed by said rotating box and said fixed base in the factory, and a long tail 237 of said aluminum foil film 236 should be folded back at this time, leaving a short portion of said long tail 237 outside the perfume box. Immediately before starting to use the perfume box, the consumer may pull the short portion of said long tail 237 so as to tear off the aluminum foil film 236 while keeping the perfume box inside the rotating box.

Figure 14:
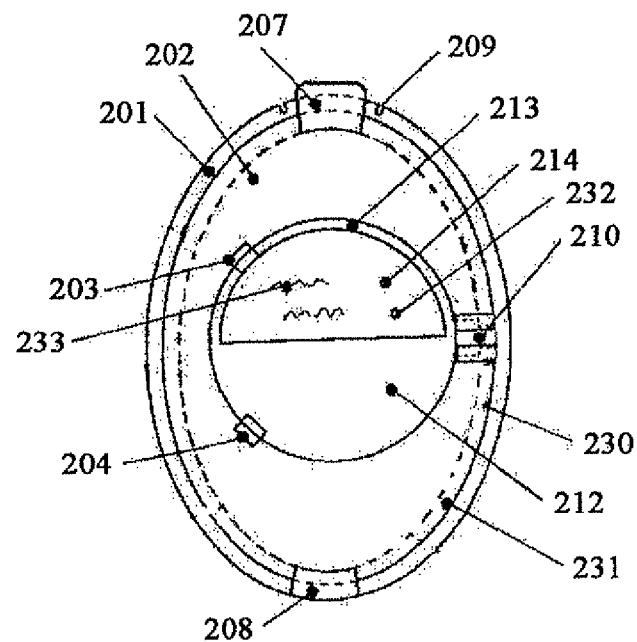
FIG. 14(a) and FIG. 14(b) are schematic views of a structure of an air freshener of a second embodiment of the present invention.
Figure 14:
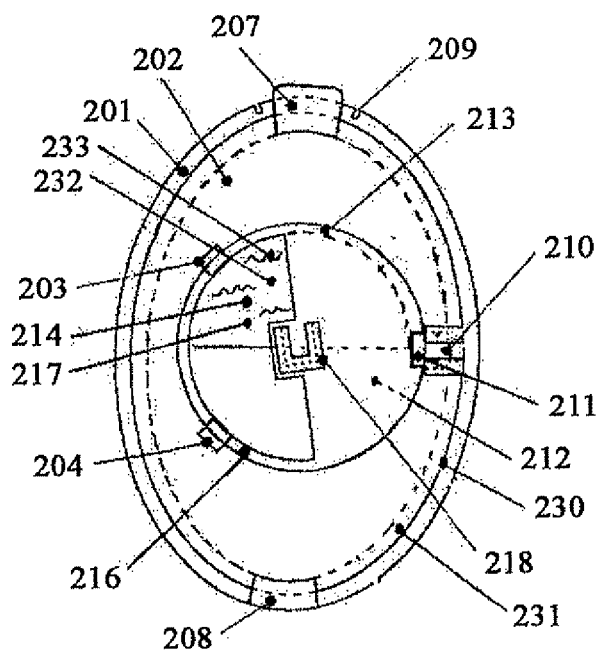

As shown in FIG. 14(a), when assembling the air freshener of the second embodiment of the present invention, said front cover 201 should be firstly placed with its back side (as shown in FIG. 8(b)) facing upward, i.e. an opening of said front cover 201 facing upward, and then the perfume box is placed thereon (the aluminum foil film 236 of the perfume box has been torn off). The box body 230 of said perfume box faces downward, the semipermeable film 232 of said perfume box faces upward, and the edge 231 of the box body 230 of said perfume box is just embedded into the step 205 and step surface 206 of said front cover 201. And then the rear base 202 of said rotating box is also embedded into the step 205 and step surface 206 of said front cover 201 with its front side (FIG. 9(a)) facing downward and with its back side (as shown in FIG. 9(b)) facing upward. When the rear base 202 is inserted, one end of said rear base 202 should be firstly clipped inside the fastener 208 of said front cover 201, the fastener 207 is pulled to provide a position for said rear base 202 to be entirely embedded, and then the fastener 207 is loosened, thereby the clipping of said rear base 202 is completed. At this time, the perfume box can be viewed from the air holes 214 of said rear base 202. As shown in FIG. 14(b), when assembling the air freshener of the second embodiment of the present invention, the fixed base 216 is embedded into the round groove 213 of said rear base 202 with its back side (FIG. 10(a)) facing upward. Firstly, one end of said fixed base 216 abuts against the fixed fasteners 203 and 204, and the other end of said fixed base 216 is entirely embedded, and then the latch 211 is inserted into the movable fastener 210 to ensure the clipping of said fixed base 216. Finally, the clip head 24 of the fixing device (the fixing clip 22 and the suction cup 23) is embedded into the clipping groove 218 of said fixed base (not shown in the drawings), so as to complete the assembling of the air freshener of the second embodiment of the present invention.

When said fixed base 216 is fixed on the smooth surface, such as a surface of window glass inside a car, or any smooth surface inside a room, through the fixing device (the fixing clip 22 and the suction cup 23), the rotating box which consists of the front cover 201, the rear base 202 and the embedded perfume box can be rotated so as to change the overlapping area between the air holes 214 and the air holes 217, thereby to adjust the release amount of the perfume vapor.

In the above specific embodiment, the external contour of said front cover 201 and said rear base 202 is substantially in elliptical shape, this is only one example, however they may be other geometrical shapes (for example, a polygon, not shown in the drawings) or other esthetical shapes (for example, a shape of an animal or a flower not shown in the drawings) on the premise that a sufficient space must be left for the round groove 213 to be opened in a suitable part (a central part as shown in FIG. 9(b); other parts also acceptable, although not shown in the drawings) of said rear base 202 for receiving said circular fixed base 216, and for said rear base 202 to be rotated (not shown in the drawings).

While in the above specific embodiments, the protruding surface of said front cover 201 is smooth, this is only one example, and the protruding surface of said front cover 201 may be configured to be a constitution of various esthetical shapes (for example, a constitution of a shape of an animal or a flower, not shown in the drawings) on the premise that the configured shape of the protruding surface of said front cover 201 must cause said front cover 201 to be interbedded and assembled with the box body 230 of said perfume box (not shown in the drawings).

While in the above specific embodiments, said rear base 202 has the fasteners 207 and 208, said fixed base 216 has the fasteners 203, 204 and 210, this is only one example, and it is a matter of course that other alternative methods can be employed, for example, the method in which a "sliding-in and back-buckling" fastener can be made there-between for clipping said rear base 202 and said fixed base 216 (not shown in the drawings) on the premise that: (1) said rear base 202 can be embedded into said front cover 201, and be opened and removed (not shown in the drawings), and (2) said fixed base 216 can be embedded into the round groove of said rear base 202, so that the rotating box formed by the front cover and the rear base can rotate with respect to the fixed base (not shown in the drawings). The perfume used in the perfume box of the air freshener of both the first embodiment and the second embodiment of the present invention may be a perfume dispensed with various aromatic raw materials in accordance with a formulation in a perfume factory, or a scent obtained by diluting the perfume according to a certain proportion, and the dilution solvent is generally ethanol or isopropyl alcohol. A dye can also be added into the perfume or scent housed in the perfume box so as to make the perfume or scent appear in different colors which substantially indicate the types of the fragrance, for example, red indicates the fragrance of strawberry, pink indicates the fragrance of rose, purple indicates the fragrance of lavender and yellow indicates the fragrance of lemon etc. In addition, a trademark or esthetical patterns may be made or imprinted on external surfaces of said rotating box, said fixed base and said perfume box.

Even though only preferable embodiments are selected to illustrate the present invention, a person skilled in the art should clearly realize that various modifications and alterations could be made to the present invention without departing from the scope which is defined by the claims appended herein. For example, the size, the shape, the position or the orientation of various components can be changed according to specific requirements and/or expectations. A function of one element could be completed by two elements, and visa versa. Structure and function of one embodiment could be adopted by another embodiment. For example, the various structures or assembling manners in a first embodiment could be applied to a second embodiment, and visa versa. All advantages are not necessarily available for a specific embodiment simultaneously. Each feature distinguishing from the prior art, whether solely or combined with other features, should be deemed as the further sole description of the present invention by the applicant, including the structural and/or functional concept for implementing this feature. Therefore, the above description about each embodiment of the invention is only illustrative, but not restrictive, and it should be understood that the present invention is defined by the appended claims and their equivalents.

What is claimed is:

1. An air freshener, comprising:
a rotating box;
a fixed base mounted on said rotating box which can rotate with respect to said fixed base;
a perfume box filled with a liquid perfume, said perfume box can rotate together with said rotating box; and
a fixing device, wherein
said rotating box comprises a front cover and a rear base with a circular groove, said rotating box can receive and place therein a circular sheet of said fixed base such that the rotating box can rotate with respect to the fixed base, and has a shape of a front cover opposite to the opened side thereof which form a space for receiving a box body of said perfume box and inter-embed a convex-concave shape of the box body of said perfume box into said space for rotating the perfume box together with the rotating box,
said fixed base comprises said circular sheet which matches with the circular groove of the rotating box, and has one or more than one air hole for exposing the perfume box when said rotating box is rotated with respect to the fixed base for adjusting the releasing area of perfume vapor, and has a clipping groove built thereon for mounting the fixing device,
said perfume box has the box body suction-molded from a transparent plastic sheet with a protruding convex-concave shape which inter-matches with the shape of the front cover of the rotating box, and has a semi-permeable film which is sealed onto a plane of an edge of an opened end of the box body for preventing leak-out of perfume liquid and allowing diffuse-out of perfume vapor, said edge of the box body has an airtight aluminum foil with a long tail which is laminated over the semi-permeable film for preventing diffuse-out of the perfume vapor before use, when the perfume box is installed in the air freshener, said liquid perfume can be viewed through the box body of the perfume box from the direction outside the rotating box or the front cover and can be viewed through the air hole(s) and the semi-permeable film on the box body from the direction outside the circular sheet of the fixed base, and
said fixing device comprises a fixing clip or a suction cup which can be embedded to the clipping groove of the circular sheet of the fixed base for fixing the air freshener onto a grille or a smooth surface, respectively, wherein said front cover of the rotating box has an opened side and a recessed step and a step surface around the periphery of the opened side for receiving and placing therein the rear base together with the edge of the box body of the perfume box, and has a shape opposite to the opened side which form a space for receiving said box body of said perfume box and inter-embed a protruding surface of the box body of the perfume box for rotating the perfume box together with the rotating box,
said rear base of the rotating box has an inter-matching external shape with the recessed step and step surface of the front cover and has a circular groove for receiving and placing therein the circular sheet of the fixed base, and an air hole is provided on said circular groove for exposing said perfume box.

2. The air freshener of claim 1, wherein
said fixing clip of the fixing device comprises a clip tooth and a clip head, and said suction cup of the fixing device comprises a vacuum suction cup and a clip head.

3. The air freshener of claim 1, wherein
said front cover and said rear base of the rotating box are connected by fasteners, and said circular groove of the rear base and said circular sheet of said fixed base are connected by fasteners.

4. The air freshener of claim 1, wherein
the external shape of the periphery of said front cover and said rear base of the rotating box and said box body of the perfume box is elliptic.

* * * * *